United States Patent [19]
Smith

[11] Patent Number: 5,277,700
[45] Date of Patent: Jan. 11, 1994

[54] FACIAL BANDAGE

[76] Inventor: Veronica C. Smith, 2951 60th Ave., Oakland, Calif. 94605

[21] Appl. No.: 859,592

[22] Filed: Mar. 23, 1992

Related U.S. Application Data

[63] Continuation of Ser. No. 597,883, Oct. 12, 1990, abandoned.

[51] Int. Cl.$^5$ ............................................. A61F 13/12
[52] U.S. Cl. .................................. 602/74; 602/75; 2/DIG. 11
[58] Field of Search .................. 602/74–78, 902 2/DIG.11, 181; 128/402

[56] References Cited

U.S. PATENT DOCUMENTS

| | | | |
|---|---|---|---|
| 1,313,138 | 8/1919 | Thomas | 602/78 |
| 1,607,717 | 11/1926 | Nagler et al. | 602/74 |
| 1,908,669 | 5/1933 | Horne | 128/163 |
| 3,054,400 | 9/1962 | Lizio | 128/163 |
| 3,141,459 | 7/1964 | Orcutt | 602/78 |
| 3,541,608 | 11/1970 | Otwell | 602/74 |
| 3,759,256 | 9/1973 | O'Malley | 128/89 A |
| 4,131,953 | 1/1979 | Kimotsuki | 2/171.1 |
| 4,502,476 | 3/1985 | Welt | 602/74 |
| 4,658,811 | 4/1987 | Beaird | 602/78 |
| 4,765,338 | 8/1988 | Turner et al. | 128/402 |
| 4,907,580 | 3/1990 | Leonardi | 602/74 |
| 4,944,289 | 7/1990 | Matthews | 128/163 |
| 5,020,536 | 7/1991 | Keen | 128/163 |

FOREIGN PATENT DOCUMENTS

| | | | |
|---|---|---|---|
| 0389777 | 8/1922 | Fed. Rep. of Germany | 128/163 |
| 0761588 | 5/1934 | France | 128/163 |

OTHER PUBLICATIONS

Gershmann, Journal of A.M.A. vol. 168, No. 7 Oct. 18, 1958.

*Primary Examiner*—Randall L. Green
*Assistant Examiner*—Rob Clarke
*Attorney, Agent, or Firm*—Owen, Wickersham & Erickson

[57] ABSTRACT

An adjustable facial dressing for compression and/or support of facial features for medical treatment is disclosed. A main band elastic can be positioned on the face (head or neck) in various positions by adjusting the position of an integral hook tape tab at any position along the main band. A separate anchor strap has hook tape tabs at its ends. The hook tape tabs each engage one of two generally opposite sides of the main band around only one side of the face (head or neck). The anchor strap hook tape tabs can engage the main band at any position along the main band, to thereby provide compression or support of the face/head/neck area covered and assist in maintaining the position of the main band on the face. More than one anchor strap may be used.

1 Claim, 4 Drawing Sheets

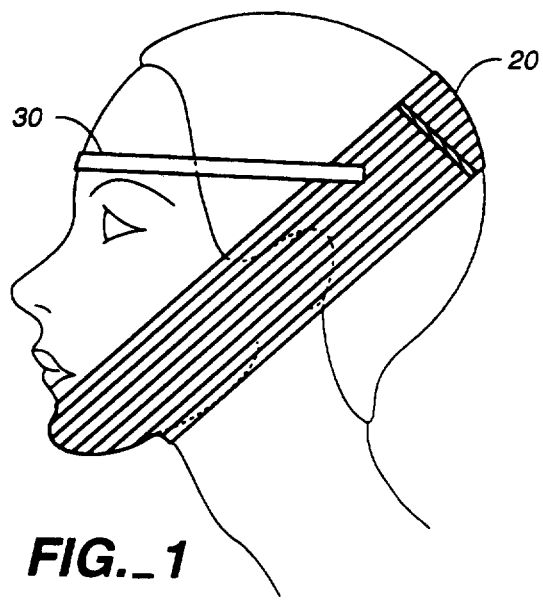
FIG._1
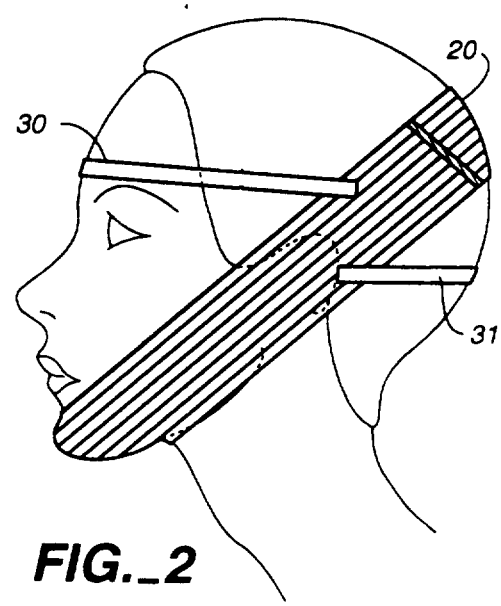
FIG._2
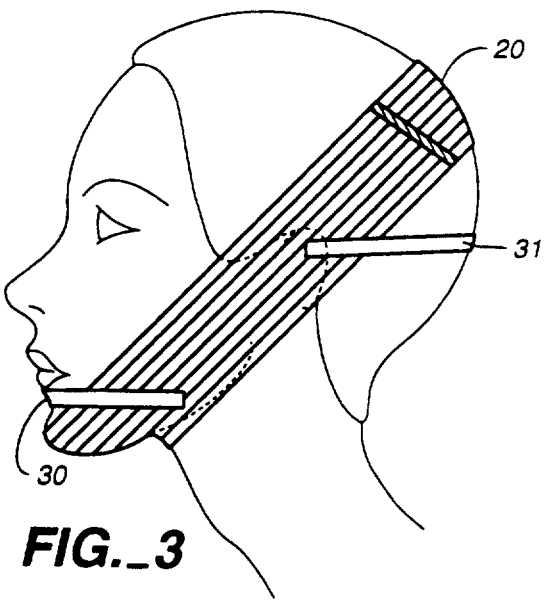
FIG._3
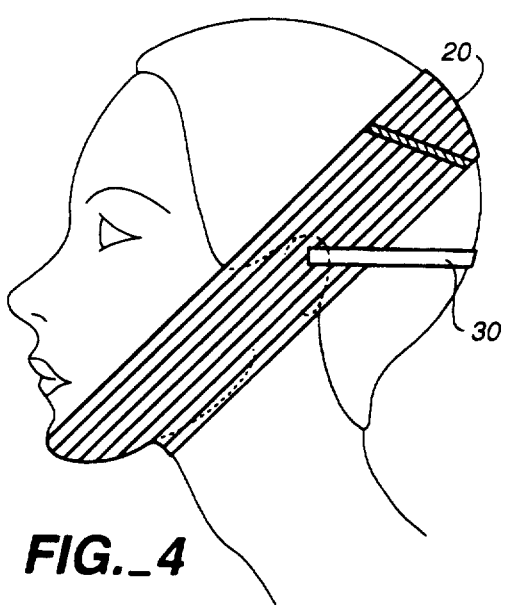
FIG._4

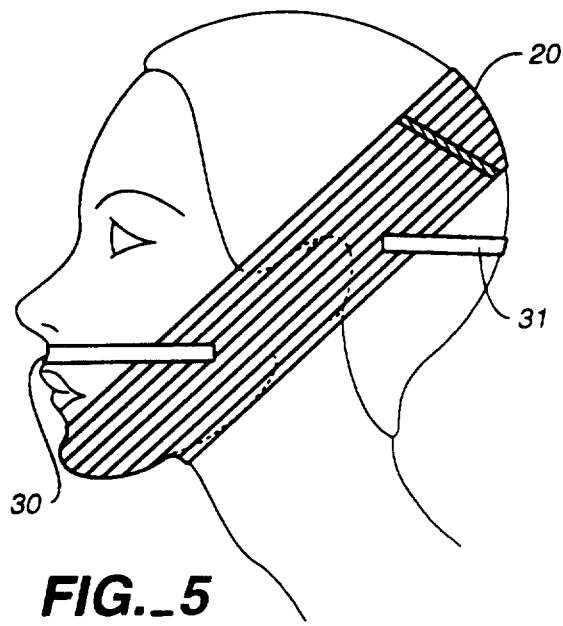
FIG._5
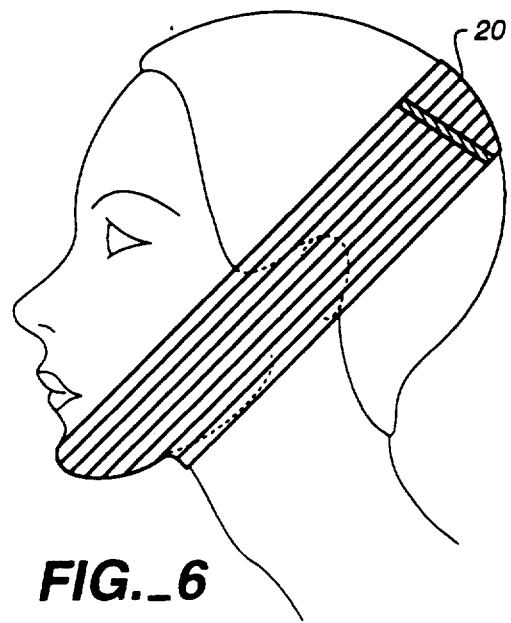
FIG._6
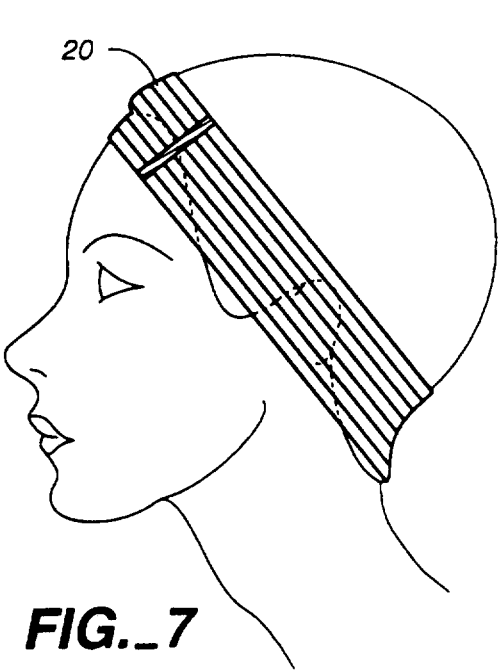
FIG._7
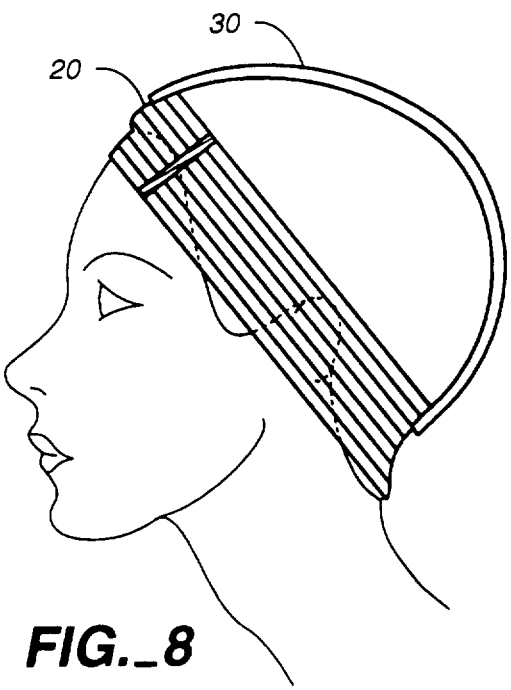
FIG._8

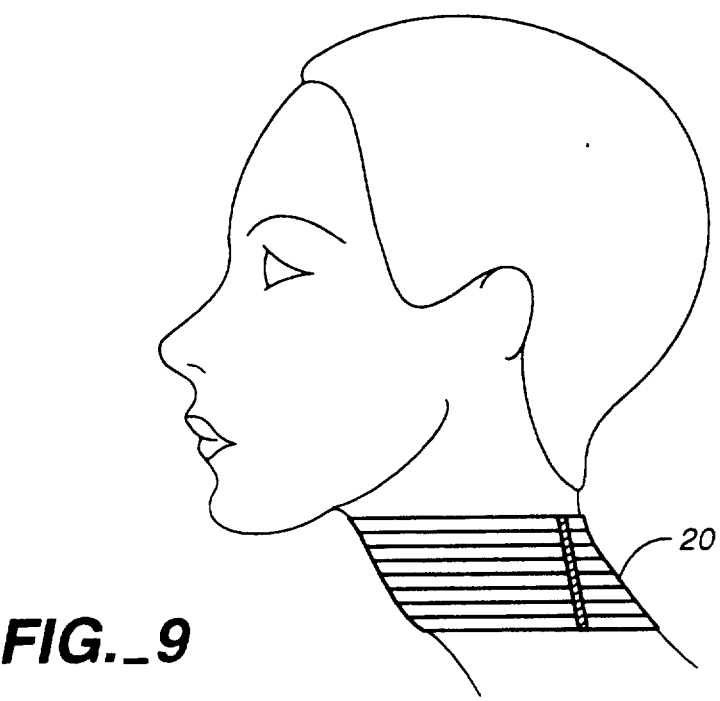
FIG._9
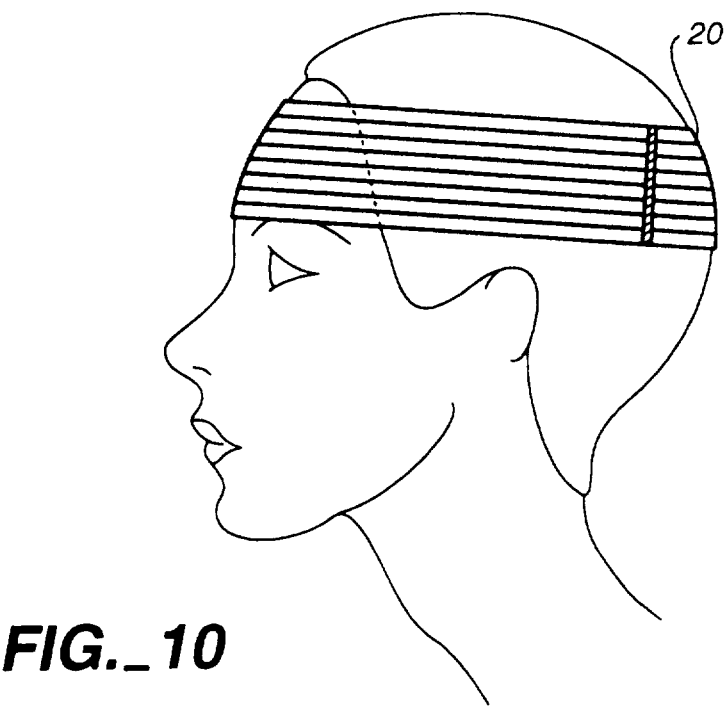
FIG._10

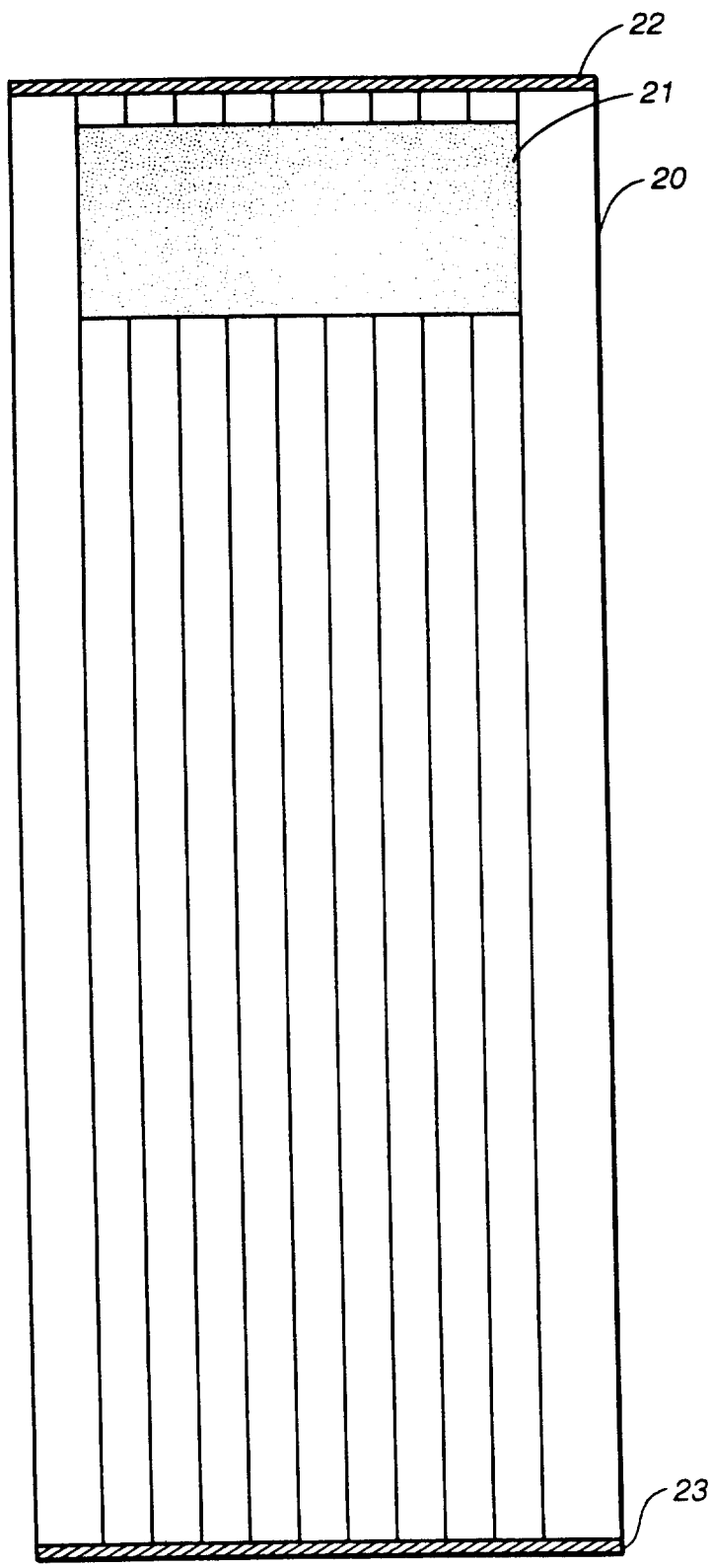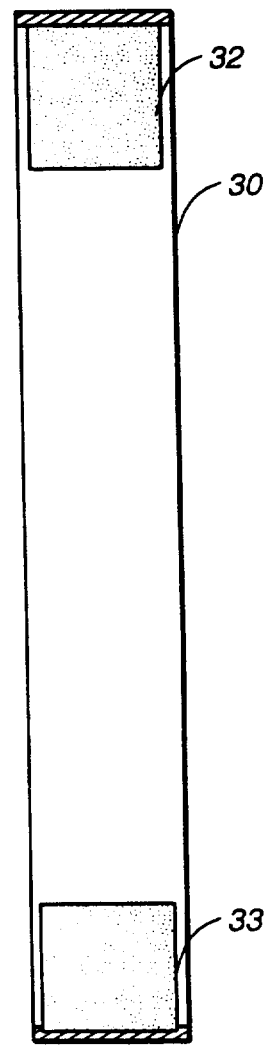
FIG._11
FIG._12

FACIAL BANDAGE

This application is a continuation of application Ser. No. 07/597,883, filed Oct. 12, 1990 filed Nov. 12, 1990 now abandoned.

BACKGROUND OF THE INVENTION

This application relates to the field of medical garments for the face/head/neck.

SUMMARY OF THE INVENTION

The invention is an adjustable facial dressing designed for compression and support. A band is worn in various positions on the face (head and neck) and has one or two anchoring straps.

BRIEF DESCRIPTION OF THE DRAWINGS

FIGS. 1, 4, and 8 show various positions of an embodiment of the invention as worn on a face (head and neck);

FIGS. 2, 3, and 5 show various positions of another embodiment of the invention as worn on a face (head and neck);

FIGS. 6, 7, 9, and 10 show various positions of a part of an embodiment of the invention as worn on a face (head and neck);

FIG. 11 shows a band of an embodiment of the invention; and

FIG. 12 shows an anchor strap of an embodiment of the invention.

DETAILED DESCRIPTION

In FIG. 1 the band 20 is worn over the chin and over the top of the head with an anchoring strap 30 across the forehead.

In FIG. 2 the band 20 is worn over the chin and over the top of the head with two anchoring straps 30,31, one across the forehead and one across back of the head.

In FIG. 3 the band 20 is worn over the chin and over the top of the head with the two anchoring straps, 30,31 one under the bottom lip and one across back of the head.

In FIG. 4 the band 20 is worn over the chin and over the top of the head with the anchoring strap 30 across the back of the head.

In FIG. 5 the band 20 is worn over the chin and over the top of the head with one anchor strap 30 worn above the upper lip and the other anchor strap 31 worn across back of head.

In FIG. 6 the band 20 is worn over the chin and over top of the head.

In FIG. 7 the band 20 is worn behind the head at the neck and across the forehead.

In FIG. 8 the band 20 is worn behind the head at the neck and across the forehead with the anchor strap 30 over the top of the head.

FIG. 9 shows the band 20 worn wrapped around the neck.

FIG. 10 shows the band 20 worn over the forehead.

FIG. 11 shows an embodiment of the band 20. It is a mono-filament nylon, polyester, rubber elastic approximately 22" to 29" long and 2.5" to 3.5" wide with a hook tape tab 21 sewn at one end.

FIG. 12 shows an embodiment of the anchor strap 30 which is a plush back elastic ¾" to 1.5" wide with hook tapes 32,33 sewn on both ends.

An embodiment of the invention as shown in FIG. 11 includes an adjustable facial band 20 approximately 2.5" to 3.5" wide and 22" to 29" long. Each end is overlocked with a wooly nylon thread 22,23. On one end a 2"×2" to 3"×3.5" strip of hook tape (tab) 21 is sewn down. This hook tape tab 21 attaches anywhere on the band 20 (as a closure). The band 20 is made of a monofilament elastic of polyester, rubber and nylon and is plush on both sides. Embodiments of the invention include the band 20 with one or two elastic straps 30,31 each approximately ¾" to 1.5" wide and 10" to 13.5" long. Both ends of each strap 30,31 are turned down about ¼" with a strip of hook tape (tab) (e.g. 32,33) ¾" to 1.5" long sewn down. The straps 30,31 are a crucial aspect of the design and anchor the band 20 in position and serve as support for the band. The straps 30,31 can be placed anywhere on the band 20 by the hook tape tabs (e.g. 32,33). The embodiments of the adjustable facial dressing provide facial support and compression. The embodiments of the facial dressing can be worn in various positions on the face/head/neck as shown in FIGS. 1-10. The embodiments of the facial dressing provide one or two anchor straps.

The facial dressing is used for an array of procedures. It is designed to support and/or give compression to different areas of the face (head and neck). By making minor adjustments with the band 20 and strap 30 it is ideal for the following:

| | |
|---|---|
| Antisnoring Support | Maxillofacial Surgery |
| Chin Augmentation | Oral Surgery |
| Compression Dressings | Otoplasty |
| Coronal Lift | Parotid Gland Surgery |
| Dental Extraction Surgery | Platysmal Neck Cont. |
| Facelift | Submandibular Lipectomy |
| Facial Liposuction | Submandibular Liposuction |
| Genioplasty | Submentoplasty |
| Hair Transplant | TMJ Arthroscopy |
| Mandibular Osteoplasty | Temporomandibular Joint |
| Mandibular Surgery | Surgery. |

I claim:

1. An adjustable facial dressing comprising:

an elastic flexible band being adapted to encircle a face (head and neck) substantially conforming to the shape thereof in one of a plurality of a substantial variety of various positions;

said band made of a material having at least one plush side operable to mechanically interlock with a hook fastener material;

a section of hook fastener material mounted adjacent a first end on one side of said band; and said section of hook fastener material arranged and constructed to overlie and mechanically interlock with the plush side of the band at any location there along when the first end portion of the band with hook fastener material mounted thereon is superposed in overlying position on the plush side to make a closed looped bandage around the face of the user;

at least one elastic flexible strap separate from said band and defining first and second ends;

a section of hook fastener material mounted on each said first and second ends on a common side of said strap;

said sections of hook fastener material arranged and constructed to mechanically interlock at any point along the continuous plush surface of the band merely upon manually pressing the hook fastener material mounted at either end of the strap into contact with any part of the plush side of the band whereby opposite ends of the strap can be detachably fastened to opposite sides of the band at any preselected point throughout the continuous length of the plush surface side of the encircling band;

the mechanical interlocking between the sections of fastener material mounted at opposite ends of said strap and the plush side of said band consisting the sole means of attachment of said strap to said band.

* * * * *